United States Patent [19]
Reynnells et al.

[11] Patent Number: 6,029,080
[45] Date of Patent: Feb. 22, 2000

[54] METHOD AND APPARATUS FOR AVIAN PRE-HATCH SEX DETERMINATION

[76] Inventors: Richard D. Reynnells, 8036 Sandy Springs Rd., Laurel, Md. 48864; Cal J. Flegal, 2351 Mt. Hope Rd., Okemos, Mich. 20707

[21] Appl. No.: 09/110,782

[22] Filed: Jul. 6, 1998

Related U.S. Application Data

[63] Continuation of application No. 60/052,074, Jul. 9, 1997.

[51] Int. Cl.[7] .......................................... A61B 5/05
[52] U.S. Cl. ......................... 600/407; 600/410; 600/437; 356/52; 356/55
[58] Field of Search ..................................... 600/407, 410, 600/415, 420, 425, 431, 437, 476; 324/307, 309; 250/370.08; 356/52, 55, 58

[56] References Cited

U.S. PATENT DOCUMENTS

| | | |
|---|---|---|
| 3,948,765 | 4/1976 | Anschutz . |
| 3,974,624 | 8/1976 | Bentley et al. . |
| 4,681,063 | 7/1987 | Hebrank . |
| 4,895,157 | 1/1990 | Nambu . |
| 5,017,003 | 5/1991 | Keromnes et al. . |
| 5,277,320 | 1/1994 | Corkill et al. . |
| 5,402,786 | 4/1995 | Drummond . |
| 5,749,453 | 5/1998 | Doornekamp et al. . |
| 5,759,772 | 6/1998 | Kirkpatrick et al. ........................ 435/6 |

OTHER PUBLICATIONS

Westbrook and Kaut, MRI in Practice (1993) Blackwell Scientific publications, Boston, MA.

Peterson, et al, An Introduction to Biomedical Nuclear Magnetic Resonance, Eds. Thieme, Inc. New York, New York (1986).

A. L. Romanoff, Poultry Science, vol. XII pp. 305–309.

Pfeffer, P.E., et al, Nuclear Magnetic Resonance in Agriculture Eds, CRC Press, Inc. Boca Raton FL, (1989) pp. 406–424.

Wachtler, F., et al., Belgian Journal of Zoology; Third Belgian Contress of Zoology, vol. 123–Supplement 1 (Nov., 1993).

A. Lirette et al.; In Vivo Nuclear Magnetic Resonance Spectroscopy of chicken Embryos from two Broiler Strains of varying fat Content; Poultry Science 72(8):1993 Aug.; pp. 1411–1420.

*Primary Examiner*—Brian L. Casler
*Attorney, Agent, or Firm*—Ian C. McLeod

[57] ABSTRACT

The present invention provides a non-invasive method and apparatus (44) for sexing members of the avian species in the egg (26). Further, the present invention when in combination with an egg sorter (28) provides an automated method for sexing and sorting members of the avian species in the egg which is rapid and reliable. In particular, the method uses nuclear magnetic resonance to determine whether the live embryo within an egg contains male or female sex organs. The invention further provides an apparatus for sexing members of the avian species in the egg which comprises a conveyor (24) that transports a plurality of eggs through the apparatus (44) wherein the sex of the embryo is determined. Then the egg is transferred to the egg sorter which sorts the eggs into a first group comprising eggs containing male embryos and a second group comprising eggs containing female embryos. The present invention can further sort eggs into a third group comprising eggs which are unusable.

42 Claims, 5 Drawing Sheets

METHOD AND APPARATUS FOR AVIAN PRE-HATCH SEX DETERMINATION

This application claims the benefit as a continuation of U.S. Provisional Application No. 60/052,074 filed Jul. 09, 1997.

GOVERNMENT RIGHTS

The Government reserves the right of a non-exclusive, nontransferable, irrevocable, paid-up license to practice the invention or have practiced throughout the world by or on behalf of the Government, for any patent issuing on this invention (37 CFR 501.6(a) (1); and Title 15, U.S. Code, §3710d).

BACKGROUND OF THE INVENTION (1) Field of the Invention

The invention relates to a method and apparatus for pre-hatch avian embryo sex determination. In particular, the invention relates to a non-invasive method and apparatus for determining the sex of avian species while in the egg and sorting the eggs into groups consisting primarily of either male or female embryos, and other groups consisting of eggs that are unusable. The invention uses a non-invasive imaging method, such as nuclear magnetic resonance, to make the sex determination.

(2) Description of the Related Art

Sex separate rearing is an important component for much of the broiler and essentially all egg layer and turkey production. Essentially all commercial hatcheries of pullets that will become table egg laying hens and commercial turkey hatcheries use sex separate rearing of flocks, and approximately 15–30% of the commercial hatcheries producing broilers use sex separate rearing of flocks. Depending on hatchery output and production and processing/marketing requirements, and cost relationships sex separate rearing can be of economic benefit to poultry producers.

Currently, there are three methods available for sexing poultry. Day-old chicks can be sexed either by vent sexing, or feather sexing methods. Alternatively, male and female chicks can be reared together until secondary sex characteristics become apparent, then the chicks can be separated based on sex and reared separately.

Vent sexing relies on the visual identification of sex based on the appearance of sex related anatomical structures. Vent sexing of chicks at hatching has complications that make it more difficult than sex determination of other animals. The reason is that the sex organs of birds are located within the body and are not easily distinguishable. For example, while the vent specific copulatory structures of aves can be identified by shape, there are over fifteen different shapes to consider. Therefore, vent sexing requires highly trained individuals who have undergone a difficult and lengthy training period which makes the method expensive.

Feather sexing is based on feather characteristics that differ between male and female chicks. The two commercial uses of feather sexing are down color pattern, and rapid/slow rate of growth of the wing feathers, with the rapid feathering gene being used extensively. The method is relatively easy to learn, however feather appearances are determined by specially selected genetic traits that must be present in the chick strain. Most strains (breeds) of chickens have these feather sexing characteristics but turkeys and other aves may not, so feathering of both sexes appear identical. Therefore, feather sexing is not available for sexing in many poultry operations.

The third method of sexing chickens relies on the appearance of natural secondary sex characteristics. In males, the combs and wattles will become larger than those on females and the head will become more angular and masculine looking. The female will remain smaller than the male and is more refined in appearance. In some breeds, the feathers of each sex will develop a characteristic color pattern which facilitates sexing. Sexing based on secondary sex characteristics can usually be performed after the chicks reach four to six weeks of age.

The disadvantages of vent sexing include the difficulty in identifying the sex of a bird and the need for highly skilled personnel to make the individual vent sexing decisions which makes the method expensive. While easier to perform, feather sexing has the disadvantage of being limited to specific genetic crosses of birds. However, maintenance of genetic capacity to allow feather sexing places added constraints on breeding programs that could be reduced if a non-invasive procedure of sex determination was used. Sexing by secondary sex characteristics is the easiest method to perform but has the disadvantage of requiring birds of both sexes to be reared together for the first four to six weeks after hatch which because of feed costs and feed conversion considerations can be more expensive to the hatchery than the expense of vent sexing.

In the United States it presently costs approximately $10 million dollars a year to sex 230 million chicks destined for table egg layer operations at a cost of $0.04 to $0.05 per female chick. At a reasonable estimate of 20% of broilers also being reared sex separate, and with most chicks being feather sexed, and a cost of $0.0075 per feather sexed chick, the cost to the broiler industry is about $9 million. Vent sexing costs are much greater than feather sexing costs because of the need for highly skilled personnel. The turkey industry utilizes vent sexing for the more than 300 million poults produced annually, which represents a cost to the industry of about $12 million. Therefore, the total cost of bird sexing to the United States poultry industry probably exceeds $30 million dollars a year.

Clearly, the commercial hatchery industry has a need for a method that would allow birds to be sorted by sex that did not rely on highly skilled individuals or on using specific genetic of crosses birds.

SUMMARY OF THE INVENTION

The present invention provides a method and apparatus for determining the sex of avian species while in the egg. The terms radiation and irradiation are used in this application in the broadest of sense. As discussed in *Nuclear Magnetic Resonance in Agriculture,* (P. E. Pheffer and W. V. Gerasimowicz 2 (Eds. CRC Press, Inc.) Boca Raton, Fla., (1989), pp. 406–413) "Chemical nuclei $^1$H, $^{10}$B, $^{13}$C, $^{14}$N, $^{19}$F, $^{31}$P, among other nuclei possess magnetic moments and exhibit alignment when placed in a magnetic field. These nuclei provide strong resonance signals while naturally occurring nuclei of oxygen and carbon give relatively weak resonance signals." Nuclear Magnetic Resonance (NMR) theory is disclosed in *Instrumental Methods of Analysis,* 5th Edition, (H. H. Willard, L. L. Merritt, Jr., and J. A. Dean, D. Van Nostrand Company, New York, N.Y., 2 (1974) wherein it is stated that: "Along with spectroscopic methods for chemical analysis and the characterization of molecules, nuclear magnetic resonance (NMR) wide-line spectroscopy techniques are useful in the study of solids" (pp. 203 and 212); "NMR 'spectroscopy' concerns radio-frequency (RF) induced transitions between quantized energy states of magnetic nuclei that have been oriented by magnetic fields" (p. 203); and "NMR instrumentation involves six basic units: (1) a magnet to separate the nuclear spin energy state, (2) a transmitter to furnish RF-irradiating energy, (3) a sample probe process of the nmr signals, (4) a detector to process the NMR signals, (5) a recorder to display the spectrum, and (6) a sweep generator for sweeping the magnetic field through the resonance region to produce the spectrum" (p. 207). Although the NMR technique comprises the method of the present invention, any other method that allowed construction of images of the internal structures of the embryo, with subsequent sex determination decisions made from those images are anticipated by the present invention.

The method uses an irradiation identification method, such as nuclear magnetic resonance (NMR), to determine whether the live embryo within an egg contains male or female sex organs. The method comprises irradiating the eggs with waves of radiation without damaging the embryo which produces a detectable signal from the sex organs. The method further provides for the sorting of the eggs that have been determined to contain female embryos from the eggs that have been determined to contain male embryos. The method can further distinguish viable eggs from non-viable eggs. The invention further provides an apparatus for determining whether an egg contains a male or female embryo. The apparatus comprises a conveyor that conveys a plurality of eggs through an irradiating means which irradiates the eggs and a detecting means for capturing the signal from the sex organs of the embryo. The preferred irradiating means is nuclear magnetic resonance. After analysis of the detected signal, the apparatus then sorts the eggs into a first group comprising eggs containing male embryos and a second group comprising eggs containing female embryos. The apparatus can further sort eggs into a third group comprising eggs that are non-usable and potentially another group for reprocessing.

OBJECTS

It is therefore an object of the present invention to provide a non-invasive radiation detecting method and apparatus for sexing avian species in the egg. Further, it is an object of the present invention to provide a method which can be automated and which is rapid and reliable. Further still, it is an object of the present invention to provide a method which is non-labor intensive. These and other objects will become increasingly apparent by reference to the following description and the drawings.

DETAILED DESCRIPTION OF THE INVENTION

Figure 1:
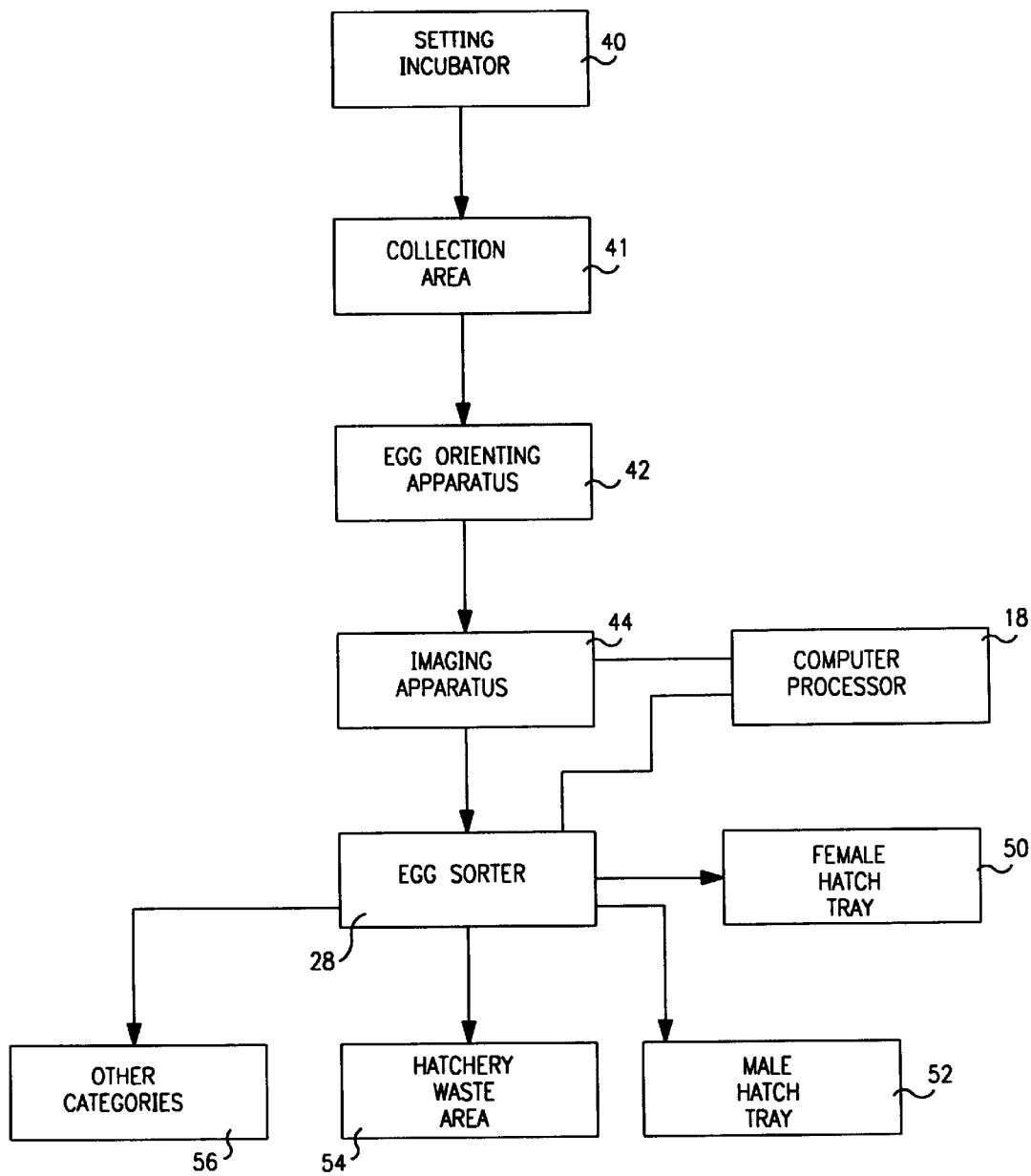
FIG. 1 is a schematic representation of the method of the invention or egg processing sequence as performed by the apparatus (FIG. 1 number 44) of FIG. 2.

The present invention provides a method for determining whether a living fertile egg contains an embryo with male or female sex organs which comprises irradiating the sex organs of the embryo while within the egg with waves of radiation without damaging the embryo to produce a detectable response, or signal hereafter referred to as a signal from the sex organs of the embryo. The sex of the embryo is determined from the signal emitted from the embryo. In one embodiment of the invention, the eggs are cooled to minimize movement of the embryo during irradiation. The eggs to be determined can be poultry eggs or eggs of other avian species.

In the method of the present invention, irradiating is accomplished by means of nuclear magnetic resonance (NMR) or magnetic resonance imaging (MRI), ultrasound, or combination thereof. The sex organs irradiated produce the detectable signal that allows male sex organs to be distinguished from female sex organs. In the preferred embodiment, the irradiating is accomplished by NMR or MRI.

In the preferred embodiment of the method of the present invention, an imaging means is provided which processes the signal which results in the electronic and immediate decision as to the category the egg and then effects the categorization of the egg, or alternatively for special cases can display an image of the sex organs of the embryo to augment sorting the eggs by machine or visual observation. The imagining means can further comprise a video screen which displays an image of the sex organs.

The present invention further provides a preferred method for determining whether a living fertile egg contains an embryo with male or female sex organs which comprises irradiating the sex organs of the embryo while within the egg with waves of radiation without damaging the embryo to produce a detectable signal from the sex organs of the embryo wherein multiples of the eggs are moved on a conveyor through an apparatus for the irradiating. In a further embodiment of the invention, the eggs are, in addition to being sorted by sex, culled for imperfect eggs and the imperfect eggs are removed from the conveyor.

The present invention further provides a preferred method for determining whether a living fertile egg contains an embryo with male or female sex organs which comprises irradiating the sex organs of the embryo while within the egg with waves of radiation without damaging the embryo to produce a detectable signal from the sex organs of the embryo wherein multiples of the eggs are moved on a conveyor through an apparatus for irradiating wherein the apparatus automatically sorts the eggs. Preferably, the apparatus can automatically sort the eggs by mechanically diverting the eggs to descrete areas or bins for delayed or immediate transfer to hatcher trays and subsequent transfer to hatcher incubators, or secondarily by lifting the eggs from the conveyor. The lifting of the eggs can be further accomplished by a vacuum cup which engages the egg to be lifted.

The present invention further provides a preferred method for sorting fertile eggs which contain either male or female embryos which comprises passively imaging the embryo in the egg so as to determine whether the embryo is male or female and sorting the eggs into male and female containing eggs based upon the imaging.

The imaging may also comprise a non-toxic material such as metals which is provided to the embryo to provide the imaging which can then be imaged by X-ray or other imaging technology such as ultrasound.

The present invention further provides a preferred apparatus for determining whether a living fertile egg contains an embryo with male or female sex organs, the apparatus comprising an irradiating means wherein waves of radiation irradiate the egg without damaging the embryo, wherein the waves produce a detectable signal from the sex organs of the embryo, and a detector means for capturing the signal from the sex organs of the egg, outside of the egg to thereby determine the sex of the egg.

The apparatus of the present invention preferably includes a conveyor mounted adjacent to the irradiating means so that multiple eggs are conveyed in sequence past the irradiating means which irradiates the sex organs of the egg.

Further still, the apparatus can comprise an egg orientating means mounted adjacent to the conveyor and prior to the irradiating means which orients multiples of the eggs in the same orientation which are then conveyed by the conveyor to the irradiating means which irradiates the sex organs of the egg. Further still, the apparatus can comprise a means to cool the eggs to minimize movement of the embryo.

The present invention further provides an apparatus for determining whether a fertile egg contains a viable embryo or an embryo with male or female sex organs which comprises a conveying means for transporting the eggs from the orientating means, an irradiating means mounted adjacent to the conveying means wherein waves of radiation irradiate the egg without damaging the embryo, wherein the waves produce a detectable signal from the sex organs of the embryo, and a detector means for capturing the signal from the sex organs of the egg outside of the egg and thereby determine the sex of the embryo.

In one embodiment, the apparatus of the present invention further comprises an egg sorting means mounted adjacent to conveying means and after the irradiating means which in response to a signal from the detector means sorts the eggs into a first group consisting of unusable eggs, a second group consisting of eggs containing male embryos, and a third group consisting of eggs containing female embryos. The egg sorting means can further comprise a vacuum cup which engages and then lifts the egg by a vacuum.

The apparatus of the present invention may further comprise an orientating means mounted adjacent to the conveyor means and before the irradiating means for orientating multiples of eggs in the same orientation.

The preferred apparatus of the present invention uses NMR or MRI to provide the signal for imaging and affecting the sorting of eggs based on sex and viability. The theory of NMR or MRI incorporated into the design and function of the apparatus of the present invention and the production and analysis of the data produced by the present invention is provided in *MRI in Practice* (Westbrook and Kaut, (1993), Blackwell Scientific publications, Boston, Mass.) and *An Introduction to Biomedical Nuclear Magnetic Resonance* (Peterson et al. Eds. (1986), Thieme, Inc. New York, N.Y.) which are herein incorporated by reference.

Definitions

RF—The term "RF" means the radio frequency band of the electromagnetic spectrum.

TR—The designation "TR" means repetition time which is the time from the application of one RF pulse to the application of the next RF pulse and is measured in milliseconds (ms). The TR determines the amount of relaxation that is allowed to occur between the end of one RF pulse and the application of the next which determines the amount of T1 relaxation that has occurred.

T1—The term "T1" means the time it takes 63% of the longitudinal magnetism to recover in the tissue.

TE—The term "TE" means echo time which is the time from the application of the RF pulse to the peak of the signal induced in the coil and is measured in milliseconds. The TE determines how much decay of transverse magnetization is allowed to occur before the signal is read which controls the amount of T2 relaxation that has occurred.

T2—The term "T2" is the time it takes 63% of the transverse magnetism to decay in the tissue.

Gradient magnetic field—The term "gradient field" means magnetic field created by passing current through a gradient coil which are coils of wire located within the bore of the magnet that alter the magnetic field in a linear fashion when a current is passed through them.

Static magnetic field—The term "static magnetic field" means the magnetic field surrounding a magnet or current conductor.

Superconducting magnet—The term "superconducting magnet" solenoid electromagnet that uses super-cooled coils of wire so that there is no inherent resistance in the system; the current flows, and therefore magnetism is generated without a driving voltage.

Solenoid electromagnet—The term "solenoid electromagnet" means a magnet that uses current passed through coils of wire to generate a magnetic field.

RF pulse transmitter—The term "RF pulse transmitter" means a coil that transmits RF at the resonance frequency of hydrogen to excite nuclei and move them into a high energy state. The coil may be a solenoid RF coil, a Helmholtz RF coil, or a surface RF coil.

Solenoid RF coil—The term "solenoid RF coil" means a coil of wire wound in the form of a cylinder. When current is passed through the coil, the magnetic field within the coil is relatively uniform. Solenoid coils are used when the static magnetic field is perpendicular to the long axis of the body being analyzed.

Helmholtz RF coil—The term "Helmholtz RF coil" means a pair of current carrying coils used to create a uniform magnetic field in the space between them.

Surface RF coil—The term "surface RF coil" means a flat coil placed over a region of interest with a selectivity for a volume approximately subtended by the coil circumference and one radius deep from the coil center.

Two dimensional Fourier transform—The term "two dimensional Fourier transform" means a form of sequential plane imaging using Fourier transform imaging. Fourier transform is a mathematical procedure to separate out the frequency components of a signal from its amplitudes as a function of time, or vice versa. The Fourier transform is used to generate the spectrum from the FID in pulse NMR techniques and is essential to most imaging techniques.

$H_o$—The term "$H_o$" is the conventional symbol used for the constant magnetic field in an NMR system.

Gx, Gy, Gz—The terms "Gx, Gy, and Gz" are the conventional symbols used for describing the gradient magnetic field. The subscripts denote the spatial direction component of the gradient.

Nuclear magnetic resonance—The term "nuclear magnetic resonance" (NMR) means the adsorption or emission of electromagnetic energy by nuclei in a static magnetic field, after excitation by a suitable RF magnetic field. The peak resonance frequency is proportional to the magnetic field, and is given by the Lamor equation. Only nuclei with a non-zero spin such as hydrogen, carbon-13, sodium-23 and phosphorus-31 exhibit NMR.

NMR signal—The term "NMR signal" means electromagnetic signal in the radiofrequency range produced by the procession of the transverse magnetization of the spins (angular momentum of the nucleus). The rotation of the transverse magnetization induces a voltage in a coil, which is amplified and demodulated by the receiver; the signal only refer only to this induced voltage.

NMR imaging—The term "NMR imaging" means the creation of images of objects such as a body by use of NMR phenomenon which is the imaging of the distribution of hydrogen nuclei (protons) in the body. The image brightness in a given region is usually dependent jointly on the spin density and the relaxation times, with their importance determined by the particular imaging technique employed.

Spin density—The term "spin density" means the resonating spins in a given region, one of the principle determinants of the strength of the NMR signal from the region.

Lamor equation—The term "Lamor equation" means the frequency of procession of the nuclear magnetic moment is proportional to the magnetic field.

Magnetic resonance imaging—The term "magnetic resonance imaging" (MRI) is equivalent to NMR.

The Pre-hatch Poultry Sex Determination method of the present invention preferably combines egg sorting technology with nuclear magnetic resonance (NMR) imaging technology to provide a means for determining the sex of an avian embryo. While the preferred method is based on NMR, any non-invasive and non-destructive imaging device, that allows for rapid and accurate determination of the embryo's sex via the presence or absence of testes, ovaries, or other sex linked attribute of the embryo, is anticipated by the present invention. For example, utilization of metallic compounds or immunological compounds that localize to specific regions in the embryo based on gender are also possible.

In commercial hatchery operations, eggs are currently incubated on flats or trays, which are with few exceptions composed of a non-porous material in setter incubators until approximately three days prior to hatch. Eggs are then either manually or mechanically transferred to open trays used in the setter incubator. After hatch, the chicks can be conventially sorted by feather sexing or vent sexing into groups comprising either all males or all females and separately reared. In the present invention, eggs are transferred to a collector spool type rollers such as those that are used in table egg grading machines or other mechanism to transfer them to the imaging apparatus. Prior to being transferred to a collection area, rotten, cracked, or otherwise defective eggs are removed. Then the eggs are pooled and transferred to hatching incubators for the final three days of incubation.

The method of the present invention provides for sex determination of the embryo after removal from the setter incubation and prior to delivery to the hatching incubators.

The imaging apparatus 44 and computer processor 18 of the present invention distinguishes male embryos from female embryos based on the presence of testes or ovaries. A male embryo has two testicles which can be discerned using NMR from a female embryo which has one ovary. As described by A. L. Romanoff (*Poultry Science* (1933), vol. XII, pp. 305–309), day-old White Leghorn chick testes measured 0.465 cm long by 0.168 cm wide, while the left ovary measured 0.620 cm by 0.313 cm wide. The right ovary in practically all cases was completely degenerated. Further, H. Hamilton, in: *Development of the Chick*. Third edition. F. R. Lillie (Ed.), Henry Holt & Co., New York, N.Y. (1952) indicated that the sex of the embryo can first be definitely determined at about the 156th hour (6.5 days) by the relative size of the two gonads (page 48) based upon dissection. On page 492, it is stated that although the right gonad of the female is greatly reduced, its medullary rudiment does not disappear completely and on page 499, it is stated that the oviduct begins to project above the surface of the mesonephros and begins the development of secondary sex characteristics. The method of the present invention anticipates that the oviduct plus ovary structural unit may represent an alternative to testes and ovary for differentiating between male and female chick embryos.

FIG. 1 shows a block diagram illustrating the preferred method for practicing the present invention. In the preferred embodiment of the present invention, the eggs are removed from the setting incubators 40 to a collection area 41 and then transferred to an orientator 42 which orients the eggs so that all eggs are in a uniform horizontal or vertical position. When the egg is oriented with the big end at the top or bottom, along a vertical plane, the egg is vertically oriented. When the poles of the egg are oriented along a horizontal axis, the egg is horizontally oriented. An example of an egg orientating apparatus is disclosed in U. S. Pat. No. 5,749,453 to Doornekamp et al which is herein incorporated by reference. In one embodiment of the invention, the oriented egg is deposited in an individual cup or pocket, similar to the cups or pockets comprising an egg grading or handling apparatus. Examples of egg handling apparatuses that can be incorporated into the method of the present invention are disclosed in U.S. Pat. No. 3,948,765 to Anschutz and U. S. Pat. No. 3,974,624 to Bentley et al and which are herein incorporated by reference.

Then the eggs either individually held within cups or pockets or between rollers or other devices comprising a conveyor means 24 (shown in FIG. 2) are transferred past the imaging apparatus 44 comprising the present invention. In the preferred embodiment the imaging means is by an NMR apparatus. The imaging means 44 irradiates each individual egg and an RF signal detector 16 (shown in FIG. 2) receives the signal from the egg. The RF signal detector 16 is connected to a computer processor 18 which processes the signal into an image that can be displayed on a video terminal 20 (shown in FIG. 2). Preferably, the image is analyzed by the computer processor 18 which interprets the signal for presence or absence of testes or ovary and for a viable embryo. To facilitate interpretation of the signal, embryonic movement can be reduced by reducing the temperature near the egg by 3 to 4 degrees F. which can be accomplished by a cooling means 30 (shown in FIG. 2) directing a flow of cool air, or other means, onto the egg.

After analysis, a sorter 28 which is activated by the computer processor 18 transfers the egg to one of four locations: a) infertile, blood ring, clear, cracked or otherwise having dead in shell embryos, are taken to the hatchery waste area 54 or other categories area 56, b) eggs containing male embryos go either to the hatchery waste area 54 or to the male hatch tray 52 for sex separate rearing, or c) eggs containing female chicks go to the female hatch tray 50. After sorting, the eggs can go to a conventional egg sizer (not shown), which sorts the eggs based on size. Sizing by weight also takes advantage of the correlation between egg size and body weight for the first two to three weeks after hatch. Minimal variation in body weight is very important in the market demand for further processed or cut-up birds. Alternatively, eggs sorted by size prior to imaging can facilitate the sex determination process by allowing the imaging device to focus on a precise area of the egg.

Figure 5:
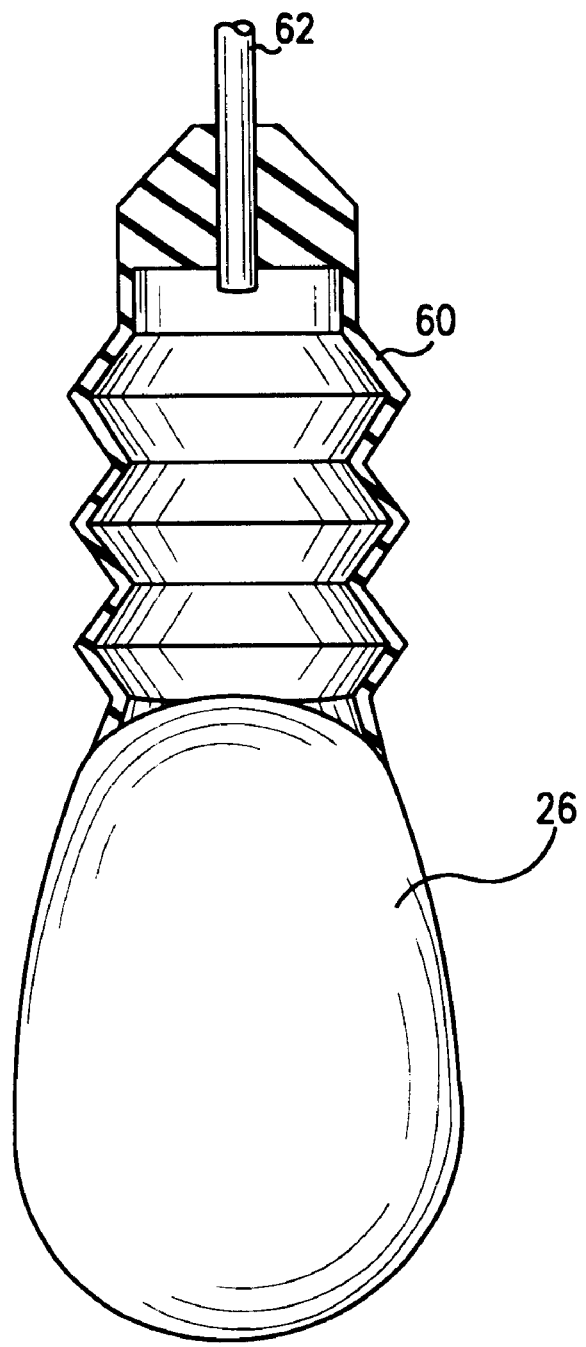
FIG. 5 shows in detail one of the suction cups in an egg sorter or lift assembly 28 or 42 that can be used for engaging and translocating an egg in the collection area prior to the egg orientating apparatus device.

An example of an egg sorter 28 suitable for incorporating into the present invention is disclosed in U.S. Pat. No. 5,277,320 to Corkill et al. which is herein incorporated by reference. Alternatively, U.S. Patent supra. to Anshutz which discloses an air jet transfer device for delivering an egg to its proper destination or U.S. Pat. No. 5,017,003 to Keromnes et al. which discloses a vacuum cup apparatus for transferring eggs either of which can be incorporated into the method of the present invention are herein incorporated by reference. FIG. 5 shows in detail a vacuum cup 60 attached by a suction conduit 62 to a vacuum source (not shown) for engaging egg 26 to be sorted. The vacuum cup can be made of a flexible composition such as rubber.

The present invention can further be used in conjunction with a mechanical vaccination injection system which is used to vaccinate the embryo prior to transfer to the hatching incubator, such a system is described in U.S. Pat. No. 4,681,063 to Hebrank which is herein incorporated by reference. Preferably, in the method of the present invention the mechanical injection system would be placed after the imaging means 44 so that there is selective injection of wanted eggs.

Figure 2:
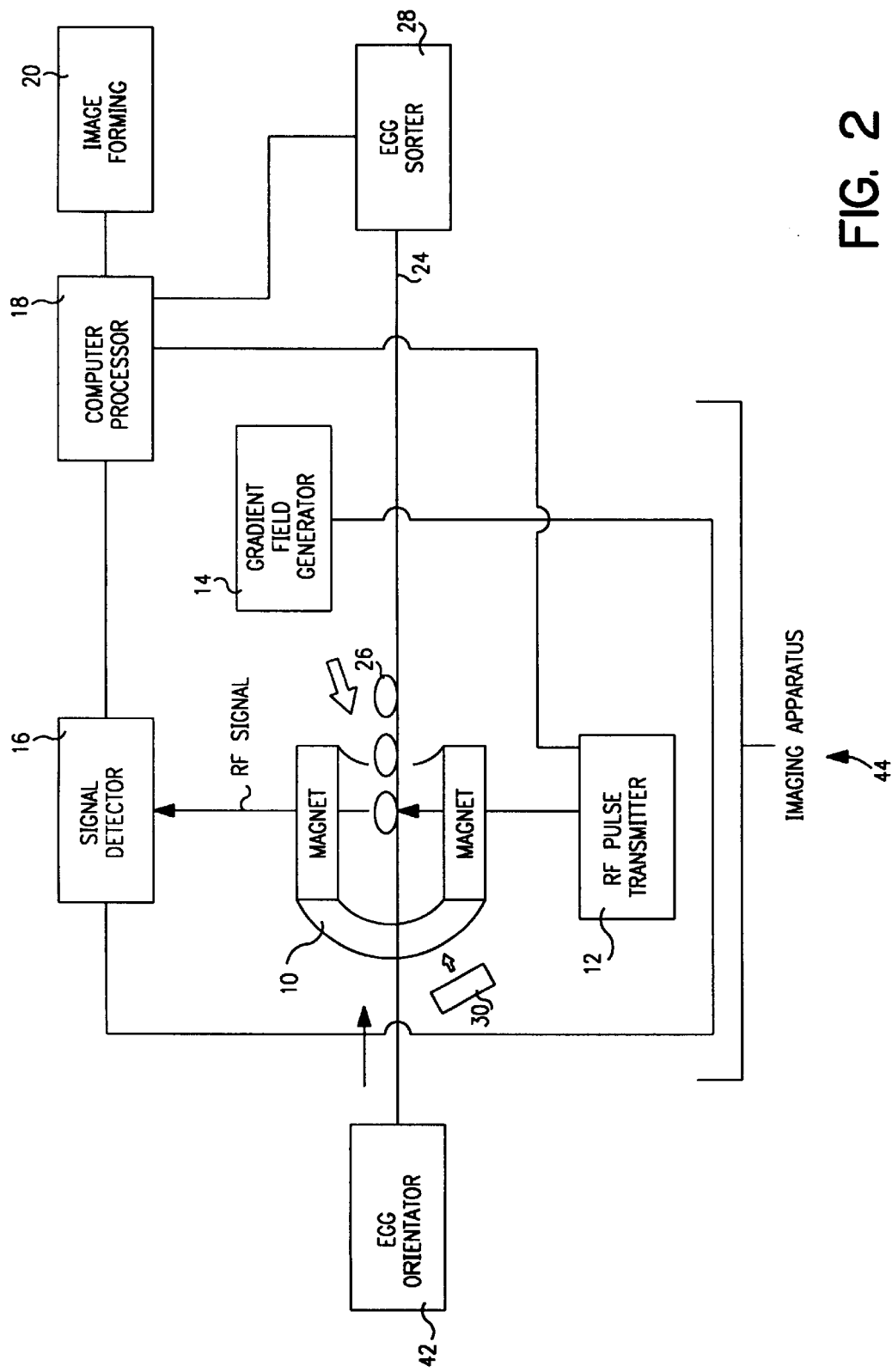
FIG. 2 includes a side cross sectional view of a cylindrical magnet 10. An NMR device in the form of a manifold arrangement (e.g., 6×8 eggs) can be created whereby multiple eggs can be processed at one time. For example, such an assembly can fit over a tray of eggs. The magnet is part of a schematic representation of other parts of the imaging apparatus of the present invention including a cooling means 30, an egg sorter with an optional lift assembly 28, and an egg orientator with an optional lift assembly 42.

The imaging apparatus 44 of the present invention is schematically shown in FIG. 2 and comprises a static magnetic field generator 10 which is a magnet having a bore that can comprise either a permanent magnet, a resistive magnet such as a solenoid electromagnet, a hybrid magnet comprising a permanent magnet and resistive magnet, or a super conducting magnet, an RF pulse transmitter 12, a gradient field generator 14 located within the bore of static magnetic field generator 10, an RF signal detector 16 which may be located within the bore of static magnetic field generator 10, a computer processor 18, an image forming section 20, and a conveyor means 24 for carrying the egg 26 past the RF pulse transmitter 12 which may be a solenoidal RF coil, a Helmholtz RF coil, or a surface RF coil located within the bore of static magnetic field generator 10. For convenience, a single coil can comprise both the RF pulse transmitter and the RF signal detector. The imaging apparatus of the present invention further comprises an egg sorter 28 and an egg orientator 42.

Static field generator 10 applies a static magnetic field $H_o$ to at least a region of the egg 26 which is positioned inside the RF pulse transmitter 12 which is within the bore of static magnetic field generator 10 including a selected portion or slice to obtain an NMR image for determining the sex of the embryo. RF pulse transmitter 12 applies to the egg an RF pulse of RF magnetic field to excite an NMR phenomenon. Gradient field generator 14 generates gradient magnetic field $G_x$, $G_y$, or $G_z$ which are superimposed on static magnetic field $H_o$. The gradient magnetic field generated by gradient field generator 14 involves, a slicing gradient field Gz for selecting and determining a slice of the egg 26, and a phase encoding gradient field Gy and a readout gradient field Gx, both for adding two dimensional information to NMR signals.

RF signal detector 16 receives and acquires an NMR signal resulting from the NMR phenomenon excited in the egg 26 and converts the signal to digital form. Computer processor 18 receives the NMR signal in digital form acquired by RF signal detector 16 to reconstruct an NMR image of the selected slice of the egg 26 by predetermined processes. The processes include, but not limited to, two dimensional Fourier transform and the two dimensional discrete inverse Fourier transform. The computer processor 18 comprises a central processing unit, consisting of instruction interpretation and arithmetic unit and fast access memory, and peripheral devices such as bulk data storage and input and output devices. Under software control, the computer processor 18 controls the RF pulses and magnetic gradients and processes the data provided by the RF signal detector 16. The computer processor 18 also controls the rate the conveyor means 24 transports the eggs through the imaging means and provides sorting instructions to the egg sorter 28. An explanation and the use of two dimensional Fourier transform and the two dimensional discrete inverse Fourier transform are provided in U.S. Pat. No. 4,895,157 to Nambu which is herein incorporated by reference. Image forming section 20 is available for visually displaying the NMR image formed by the computer processor 18 and can comprise a video screen. Interpretation of the signal received from RF signal detector 16 is performed by computer processor 18 using a predetermined process or computer program to determine whether the embryo has male or female sex organs. Based on the interpretation of the signal, the computer processor 18 activates an egg sorter 28 to sort the egg 26 according to the interpretation. The method can be performed visually but it is slower than an automated method but can be used for specialized evaluations where speed is not important.

The computer processor 18 is operationally linked to the RF pulse transmitter 12, static field generator 10, gradient field generator 14, and RF signal detector 16. Computer processor 18 in addition to analyzing the signal generated by RF signal detector 16, also synchronizes the NMR, the egg sorter 28 and the conveyor means 24. FIG. 2 shows an embodiment of the present invention wherein the eggs 26 are conveyed on a conveyor 24 past the imaging apparatus 44, however other embodiments for presenting the eggs are anticipated. For example, eggs can be conveyed in a conventional egg flat comprising a plurality of eggs in a defined array. The eggs are separately irradiated sequentially and the RF signal detected using a surface coil. Eggs 26 identified as either male or female can be removed from the flat using a sorting means comprising a plurality of vacuum cups 60 in an array corresponding to the array of eggs 26 in the flat which may require the development of new technology. The computer processor 18 activates the vacuum cups 60 to contact and engage those eggs 26 to be removed from the flat by vacuum suction. The engaged eggs 26 are lifted from the flat and transferred to another flat or to the hatchery waste area 54 by releasing the vacuum. Examples of egg sorting apparatuses that use vacuum cups to engage eggs are provided in U.S. Patents to Keromnes et al and Hebrank.

The use of NMR or other imaging means to directly ascertain the presence or absence of testicles or ovaries in an avian embryo for the purpose of sorting eggs based on sex is new. The combination of an imaging device such as NMR with a software package along with modification of egg transfer equipment from the commercial table egg or hatchery industries to selectively distribute specific eggs based on sex and viability is encompassed by the present invention and is new. Modifications of the present invention to determine presence or absence of physiological features related to sex-linked genes in embryos, or other general structural landmarks is also anticipated by the present invention.

As an alternative to an imaging apparatus based on NMR imaging, other imaging means such as ultrasound or a combination of ultrasound and NMR are anticipated by the present invention. An example of using a combination of NMR and ultrasound is in U.S. Pat. No. 5,402,786 to Drummond which is herein incorporated by reference. Such imaging means can also include use of metallic compounds that are either fed to the breeder hens (or injected into the egg), and which localize in the testes or ovary to facilitate identification of the embryo's sex as discussed above.

The present invention is expected to meet or exceed the sexing accuracy (>99%; but in some cases >95% can be adequate) and the rate (>2,200 total chicks vent sexed per hour; but a trained feather sexer may reach 3,000 birds per hour) requirements of the poultry industry. Accuracy of feather sexing is at least 97% and usually 99% or better, and accuracy of vent sexing is generally in excess of 99%. The present invention can achieve an accuracy greater that 99%. The rate of vent sexing is 1,100 to 1,200 females (2,200–2,400 total chicks) per hour per person, with six to eight people used per hatch. The present invention can achieve a rate of 13,200 to 19,200 total chicks per hour which is approximately 3.7 to 5.3 chicks per second or 0.19 to 0.27 seconds per chick. An NMR scan requires 100 milliseconds, or 0.1 seconds, per flash or pulse which is 1.5 to 3 times the speed required to meet the industry's rate requirements.

Even if the rate is slightly to the disadvantage of the industry, the improved public relations and production efficiencies would provide the incentive to utilize the present invention. Any rate disadvantage of the present invention could also be compensated for by unit financial costs less than those currently experienced.

The present invention may also be used by the duck, game bird, and pet bird or other avian industries and other animal situations where the present invention is appropriate to identify internal sexual characteristics.

EXAMPLE 1

The imaging method of the present invention can compensate for embryonic location, movement of the embryo, and structural interference to enable determination of the embryo's sex. To accomplish this, the distance between the sex organs to other structural features of the embryo in the egg were measured to determine the three-dimensional spacial relationship of the sex organs to the other structures within the embryo.

Over two hundred embryos were obtained, frozen and stored prior to evaluation. The eggs were measured length× width and weighed before embryo measurements were taken. A micrometer was used to take measurements of various embryonic structures and relate the structures to the location of the gonads. Frozen embryos were used for the measurements to stabilize the internal organs.

The normal position of the embryo is head under the right wing. The embryo measurements were, 1) the distance of the pip tooth (beak) to the center of the backbone, and 2) the pip tooth to the femur/tibia joint ("knee" joint). A cut was also made with a scalpel across the backbone connecting the relative location of the left and right femur/tibia joints. Both measurements relating to the tibia/femur joints to the backbone were estimated straight lines. The embryo's internal organs were removed. The gonads were then identified. Afterwards, the scalpel blade was pushed directly through the backbone area at the point of the femur-tibia line, which generally was close to the cephalic (head or front or top) end of the gonads. The distance from the scalpel point across the backbone was measured to determine the distance horizontally from the femur/tibia joint line to the cephalic end of the gonads. Gonad length×width measurements were taken and the values compared to expected values.

The relative distances were then used to determine the probable distance from the bottom of the egg to the middle of the gonads, and was used as a starting point during the evaluation process. This starting point, measured from the bottom of the egg, was a distance of about 62% of the egg's length. This represented the expected mid-point of the gonad location plus or minus 2 standard deviations. Table 1 shows the results of the analysis and defines the area for the expected presence of the gonads.

TABLE 1

| Measurement | Mean Distance | Standard Deviation |
| --- | --- | --- |
| Egg bottom to cephalic gonad end | 38.5165 | 2.742532 |
| Cephalic gonad end to tibia/femur joint | −1.57488* | 2.521977 |
| Pip tooth to egg bottom | 44.88326 | 3.105192 |
| Pip tooth to tibia/femur joint | 4.799531 | 2.775712 |
| Egg top to tibia/femur joint | 17.45261 | 3.288556 |

*a negative sign means that the measurement is towards the head.

EXAMPLE 2

During the NMR evaluations of the eggs, the estimated gonad middle was used as the center point for the series of imaging slices. Generally, each imaging slice was 0.5 mm thick and 1.00 mm apart. Generally 9 to 13 slices per imaging sequence were taken of the embryo within the egg, and selected images used for further analysis.

The NMR imaging system that was used for the analysis was the INOVA UNITY model manufactured by Varian Instruments and has a 4.7 Tesla, 33 cm clear bore superconducting magnet; a 20 cm clear bore, 5 Gauss/cm gradients; and a 6.25 cm RF probe. The model was used in the spin-echo imaging sequence, multi-slice mode with the following parameters: a recycle time (TR) of 1500 milliseconds, an echo time (TE) of 50 milliseconds, a field strength of 4.7 Tesla (200.5 MHz for protons), slice thickness of 1 mm, a scan time of ca. 5 minutes, a field of view of 6.4 cm×6.4 cm, an averages of 1, and a data matrix of 256×256 dots per square inch.

Figure 3:
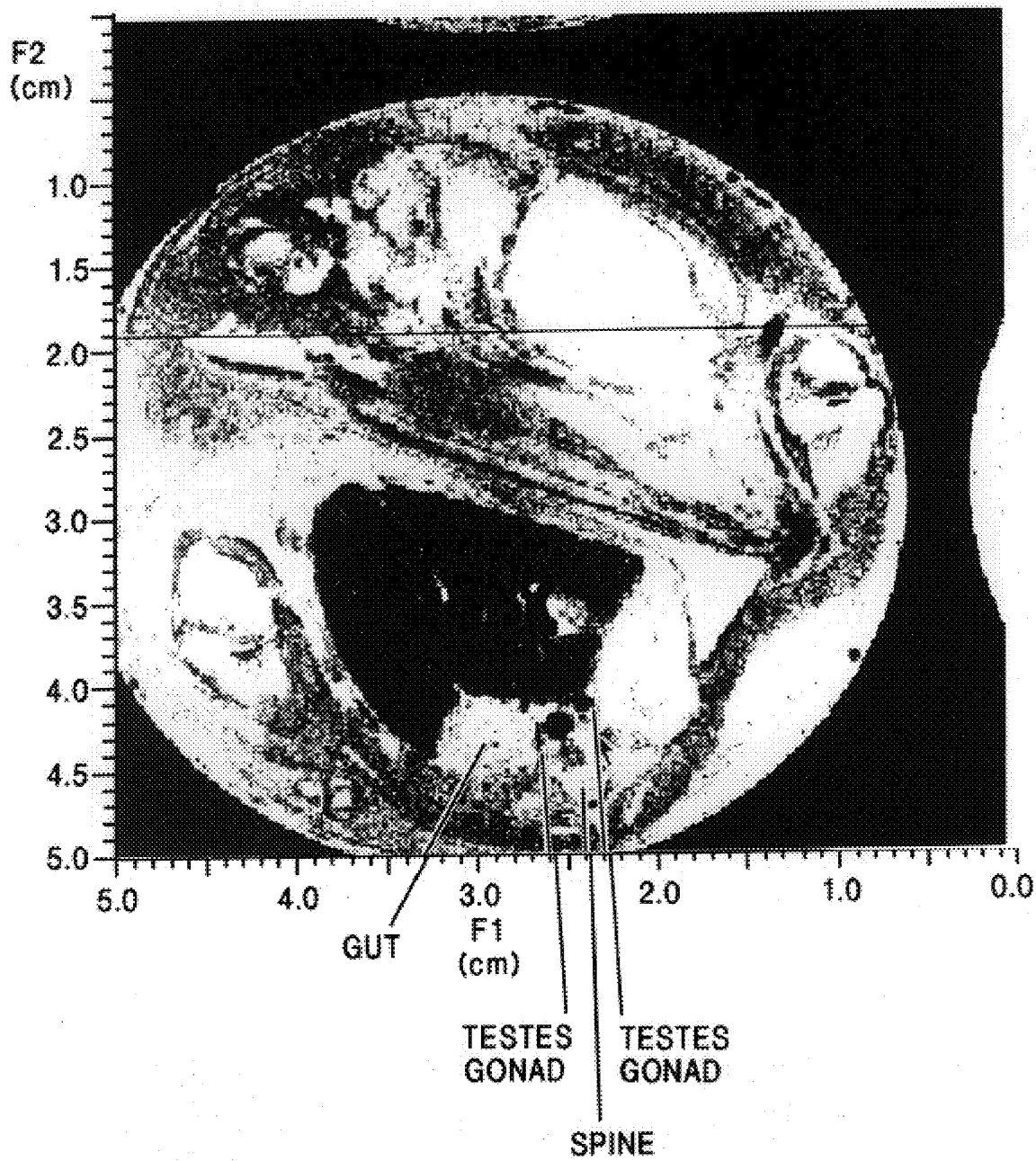
FIG. 3 shows a computer generated image produced by the method of the present invention showing the testes of a male embryo, shown in red.
Figure 4:
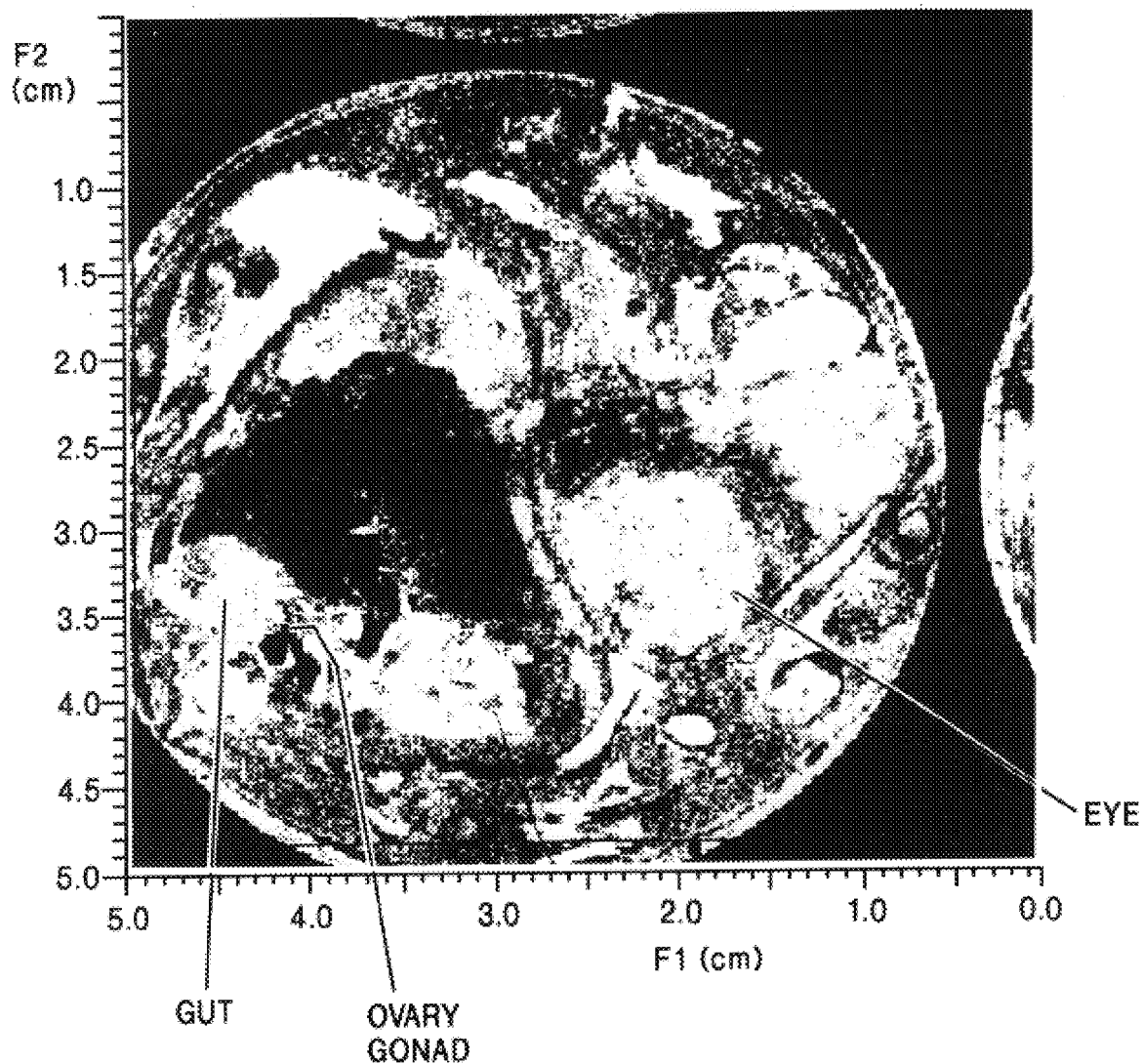
FIG. 4 shows a computer generated image produced by the method of the present invention showing the female reproductive structure/ovary of a female embryo, shown in red.

FIGS. 3 and 4 are computer generated images of turkey eggs produced by the aforementioned showing the embryo and the location of the male or female gonads. FIG. 3 shows a male embryo and the position of the two testicles. FIG. 4 shows a female embryo and the position of the one ovary.

The results further indicated that consideration should be given to using the spinal column and large intestines (e.g., lumen) as landmarks and look for other landmarks as described above which can be used depending upon the type of slice and age of the embryo.

The relatively low contrast observed between the gonads and the surrounding tissues in some images on the video terminal and the comparatively less contrast on the paper reproductions of the images indicates that a preferred embodiment of the present invention will require a multi-parameter analysis. Examples of data to be included in the multi-parameter approaches include: actual number of hours the egg was incubated prior to analysis, species of embryo (there is a difference in the relative positioning of chicken and turkey embryos in the egg), imaging contrast, gonad size and shape, and landmark location, size, and shape.

While the present invention described herein is with reference to illustrated embodiments, it should be understood that the invention is not limited thereto. Those having ordinary skill in the art and access to the teachings herein will recognize additional modifications and embodiments within the scope thereof. Therefore, the present invention is limited only by the claims attached herein.

We claim:

1. A method for determining whether living fertile eggs contain an embryo with male or female sex organs which comprises:

(a) providing a plurality of the eggs;

(b) irradiating the sex organs of the embryo with waves of radiation for each of the plurality of the eggs by movement of an apparatus producing the radiation or the eggs without appreciable physical damage to the embryo to produce a detectable signal from the sex organs of the embryo; and (c) determining the sex of the embryo of each of the eggs from analysis of the signal.

2. The method of claim 1 wherein the irradiating is by means of nuclear magnetic resonance (NMR).

3. The method of claim 1 wherein the irradiating is by means of magnetic resonance imaging (MRI) to produce a visual image of the embryo.

4. The method of any one of claims 1, 2 or 3 wherein eggs are moved on a conveyor through an apparatus for irradiating the sex organs of the embryo.

5. The method of claim 1 wherein the plurality of the eggs are moved on a conveyor through an apparatus for the irradiating of the sex organs of the embryo and wherein the apparatus automatically sorts the eggs.

6. The method at claim 5 wherein the eggs are sorted by transferring the eggs from the conveyor.

7. The method of claim 6 wherein the transferring is accomplished by a vacuum cup which engages each of the eggs to be lifted.

8. The method of claim 5 further including culling and removing imperfect eggs from the conveyor means.

9. The method of claim 1 wherein a visual imaging means is provided which processes the signal and displays an image of the sex organs of the egg.

10. The method of claim 9 wherein the imaging means is a video screen which displays an image of the sex organs of the embryo.

11. A method for sorting fertile eggs which can be either a male or female embryo which comprises (a) providing a plurality of the eggs;

(b) passively imaging the embryo in each of the eggs by movement of the eggs or an apparatus producing the imaging so as to determine whether the embryo is male or female; and (c) sorting the eggs into male and female containing eggs based upon the imaging.

12. The method of claim 11 wherein the eggs are poultry eggs.

13. The method of claim 11 wherein the eggs are provided in a conveying apparatus which repetitively indexes an egg into the apparatus for producing the imaging and then sorts the eggs.

14. The method of any one of claims 11, 12 or 13 wherein certain of the eggs are discarded.

15. The method of any one of claims 11, 12 or 13 wherein the imaging is by nuclear magnetic resonance (NMR).

16. The method of any one of claims 11, 12 or 13 further including providing a non-toxic imaging material in the eggs to provide the imaging.

17. The method of any one of claims 11, 12 or 13 further including cooling the eggs to minimize movement of the embryo.

18. An apparatus for determining whether living fertile eggs contain an embryo with male or female sex organs which comprises:

(a) irradiating means wherein waves of radiation irradiate a plurality of the eggs without damaging the embryo, wherein the waves produce a detectable signal from the sex organs of the embryo;

(b) detector means for capturing the signal from the sex organs of each of the eggs outside of the eggs to thereby determine the sex of the embryo; and (c) indexing means for moving the eggs into the irradiation and detector means or the irradiating means and detector means over each of the plurality of the eggs.

19. The apparatus of claim 18 wherein the irradiating means produces the detectable signal by nuclear magnetic resonance.

20. The apparatus of claim 18 wherein the irradiating means can produce the detectable signal by magnetic resonance imaging to produce a visual image of the embryo.

21. The apparatus of claim 18 wherein a conveyor is mounted adjacent to the irradiating means so that the a plurality of the eggs are conveyed past the irradiating means which irradiates the sex organs of each of the eggs.

22. The apparatus of claim 21 wherein a sorter for the eggs is provided adjacent to the conveyor after the irradiating means.

23. The apparatus of claim 22 wherein the sorter is a vacuum cup which engages and then lifts each of the eggs by a vacuum.

24. The apparatus of claim 22 wherein the sorter also culls imperfect eggs from the conveyor.

25. The apparatus of claim 18 wherein a visual imaging means is provided which can display the detectable signal.

26. The apparatus of claim 25 wherein the imaging means is a video screen.

27. The apparatus of claim 21 wherein an orientating apparatus for the eggs is mounted adjacent to the conveyor and forward of the irradiating means which orients the eggs in the same orientation which are then conveyed by the conveyor to the irradiating means which irradiates the sex organs of the eggs.

28. An apparatus for determining whether fertile egg contain a viable embryo or an embryo with male or female sex organs which comprises:

(a) conveying means for transporting the eggs from an orientating means;

(b) irradiating means mounted adjacent to the conveying means wherein waves of radiation irradiate the eggs without damaging the embryo, wherein the waves produce a detectable signal from the sex organs of the embryo; and (c) detector means for capturing the signal from the sex organs of the eggs outside of the eggs and thereby determine the sex of the embryo.

29. The apparatus of claim 28 further comprising a sorting means for sorting the eggs mounted adjacent to said conveying means and after the irradiating means which in response to a signal from the detector means sorts the eggs into a first group consisting of unusable eggs, a second group consisting of eggs containing male embryos, and a third group consisting of eggs containing female embryos.

30. The apparatus of claim 28 wherein said orienting means is mounted adjacent to the conveyor means and before the irradiating means for orientating the plurality of eggs in the same orientation.

31. The apparatus of claim 28 wherein the irradiating means produces the detectable signal by nuclear magnetic resonance.

32. The apparatus of claim 28 wherein the irradiating means produces the detectable signal by nuclear magnetic resonance imaging to produce a visual image of the embryo.

33. The apparatus of claim 28 wherein the irradiating means produces the detectable signal by ultrasonic waves.

34. The apparatus of claim 28 wherein the irradiating means produces the detectable signal by a combination of nuclear magnetic resonance and ultrasonic waves.

35. The apparatus of claim 29 wherein the sorting means comprises a vacuum cup which engages and then lifts each of the eggs by a vacuum.

36. The apparatus of claim 28 wherein a visual imaging means is provided which can display the detectable signal.

37. The method for sorting the plurality of the fertile eggs based on sex, the steps comprising:
   (a) irradiating each of the eggs with radiation by movement of an apparatus for producing the radiation or the egg without physical harm to the embryo to determine whether each of the eggs contain a male or a female embryo; and
   (b) sorting the eggs into groups of eggs containing male embryos and eggs containing female embryos based upon an image from the radiation.

38. The method of claim 37 wherein the radiation is produced by nuclear magnetic resonance.

39. The method of claim 37 further including sorting the eggs into viable and non-viable eggs.

40. The method of claim 37 further including transporting the eggs on a conveyor through the apparatus that provides the radiation to produce a signal that is detected by a detecting means.

41. The method of claim 37 further including sorting the eggs by a sorter for the eggs mounted adjacent to the conveyor and after the irradiating apparatus which sorts the eggs based on the sex in response to a signal from the detecting means.

42. The method of claim 37 further including orienting the eggs in the same orientation by an orientating means mounted adjacent to the conveyor and forward of the irradiating.

* * * * *